United States Patent [19]

Budge

[11] Patent Number: 5,055,599
[45] Date of Patent: Oct. 8, 1991

[54] PROCESS FOR THE HYDROGENATION OF MALEIC ANHYDRIDE TO TETRAHYDROFURAN AND GAMMA-BUTYROLACTONE

[75] Inventor: John R. Budge, Cuyahoga, Ohio

[73] Assignee: The Standard Oil Company, Cleveland, Ohio

[21] Appl. No.: 370,492

[22] Filed: Jun. 23, 1989

[51] Int. Cl.$^5$ .................. C07D 307/08; C07D 307/56
[52] U.S. Cl. .................... 549/429; 549/475; 549/508; 549/325
[58] Field of Search ............... 549/325, 429, 475, 508

[56] References Cited

U.S. PATENT DOCUMENTS

| 3,580,930 | 5/1971 | Miya et al. | 549/325 |
| 3,969,371 | 7/1976 | Michalczyk et al. | 549/508 |
| 4,048,196 | 9/1977 | Broecker et al. | 549/325 |
| 4,261,900 | 4/1981 | Härtig et al. | 549/508 |
| 4,271,080 | 6/1981 | Murib | 549/429 |
| 4,652,685 | 3/1987 | Cowse et al. | 549/508 |
| 4,965,378 | 10/1990 | Badge et al. | 549/508 |

Primary Examiner—C. Warren Ivy
Assistant Examiner—Raymond Covington
Attorney, Agent, or Firm—D. P. Yusko; M. F. Esposito; L. W. Evans

[57] ABSTRACT

Tetrahydrofuran and gamma-butyrolactone are prepared from at least one of maleic anhydride or succinic anhydride by catalytically hydrogenating vaporous maleic anhydride or vaporous succinic anhydride in the presence of hydrogen in contact with a catalyst comprising an essentially inert, at least partially porous support having an outer surface, and a catalytically active oxide material coating onto the outer surface of the support which strongly adheres to the support, wherein the catalytically active oxide material comprises the mixed oxides of copper, zinc and aluminum.

14 Claims, No Drawings

PROCESS FOR THE HYDROGENATION OF MALEIC ANHYDRIDE TO TETRAHYDROFURAN AND GAMMA-BUTYROLACTONE

BACKGROUND OF THE INVENTION

This invention relates to a catalytic process for the preparation of tetrahydrofuran and gamma-butyrolactone from at least one of maleic anhydride or succinic anhydride. More specifically, this invention relates the use of a catalyst comprising the mixed oxides of copper, zinc and aluminum wherein the catalyst is coated in a thin layer onto an inert support material.

Tetrahydrofuran is a useful solvent for natural and synthetic resins and is a valuable intermediate in the manufacture of a number of chemicals and plastics. Gamma-butyrolactone is an intermediate for the synthesis of butyric acid compounds, polyvinylpyrrolidone and methionine. Gamma-butyrolactone is a useful solvent for acrylate and styrene polymers and also a useful ingredient of paint removers and textile assistants.

It is known in the art that tetrahydrofuran and gamma-butyrolactone may be produced by a number of different methods. For example, tetrahydrofuran can be produced by the dehydration of 1,4-butanediol and gamma-butyrolactone can be prepared by the dehydrogenation of 1,4-butanediol. Specifically, most tetrahydrofuran and gamma-butyrolactone are manufactured in a multi-step sequence starting with the reaction of acetylene and formaldehyde in the presence of a cuprous acetylide complex to form butynediol. The butynediol is reduced to butanediol, which is dehydrated to tetrahydrofuran and dehydrogenated to gamma-butyrolactone as indicated above.

In addition, tetrahydrofuran and gamma-butyrolactone can be prepared by catalytic hydrogenation of maleic acid, fumaric acid and succinic acid, their respective anhydrides and ester derivatives.

The instant invention focuses on the production of tetrahydrofuran and tetrahydrofuran with gamma-butyrolactone from maleic anhydride and/or succinic anhydride. Specifically, the instant invention focuses on a fixed bed vapor phase process for the hydrogenation of maleic anhydride to tetrahydrofuran and gamma-butyrolactone in the presence of a hydrogenation catalyst.

The catalysts used in most fixed bed reactors typically are a powder which has been compressed into pellets or a slurry which has been extruded into a cylinder or other shapes and then dried. Typically, such pellets and extrudates are ⅛ inch or larger for use in commercial fixed bed reactors. It has now been discovered that such large pellets favor the production of tetrahydrofuran. An object of this invention is a fixed bed catalyst which would favor gamma-butyrolactone production.

In part, the instant invention relates to supported catalysts. The use of supports for catalysts is well known in the art. In a traditional sense, the support is normally considered to be a very small particle that provides a base for the active catalytic material. This supported catalyst is then agglomerated to provide a tablet having an essentially uniform catalyst composition throughout. The present invention is different from this art in that the catalytic material is coated onto a massive support, and a nonhomogeneous catalyst composition is obtained.

A method for coating a catalytic material onto the support or carrier is as described in U.S. Pat. No. 4,077,912. These coating techniques were used to produce a catalyst for the oxidation of n-butane to maleic anhydride in U.S. Pat. No. 4,312,787.

SUMMARY OF THE INVENTION

A fixed bed catalyst for the hydrogenation of maleic anhydride to tetrahydrofuran and gamma-butyrolactone in a continuous vapor phase process has been discovered. This catalyst favors the production of gamma-butyrolactone. The catalyst comprises an essentially inert, partially porous support having an outer surface, and a catalytically active oxide material coating on the outer surface which strongly adheres to 0 the outer surface of the support. The catalytically active oxide material comprises a mixed oxide catalyst of the formula

$$Cu_1Zn_bAl_cM_dO_x$$

wherein

M is at least one element selected from the group consisting of Groups IIA thru VA, Group VIII, Ag, Au, Groups IIIB thru VIIB, the lanthanum series, and the Actinium Series;

$0.001 < b < 500$;

$0.001 < c < 500$;

$0 \leq d < 200$; and

X is the number of oxygen atoms necessary to satisfy the valency requirements of the other elements.

DETAILED DESCRIPTION OF THE INVENTION

Maleic anhydride or succinic anhydride are hydrogenated in the vapor phase by passing a mixture of a hydrogen containing gas and the anhydride over a hydrogenation catalyst comprising the mixed oxides of copper, zinc and aluminum, which has been coated onto an inert support.

The instant process is used for the manufacture of tetrahydrofuran and gamma-butyrolactone from maleic anhydride. Some succinic anhydride may also be coproduced with the tetrahydrofuran and the gamma-butyrolactone. It has been discovered that the gamma-butyrolactone/tetrahydrofuran/succinic anhydride ratio is dependent upon the catalyst particle size. Specifically the tetrahydrofuran and succinic anhydride yields increase with increasing particle size. Conversely higher gamma-butyrolactone ratios are obtained with smaller catalyst particles.

Commercial fixed bed reactors must employ large catalyst particles (e.g. greater than 0.125 inches) to avoid big pressure drops across the bed. Consequently, a commercial fixed bed reactor using homogenous tablets or extrudate of a catalytically active oxide will favor tetrahydrofuran production with low gamma-butyrolactone yields. A practical means for reversing this product slate has been discovered. Specifically, high yields of gamma-butyrolactone may be obtained in a commercial fixed bed reactor by the coating of a thin layer of small catalyst particles onto a larger inert support.

Reactants

At least one of maleic anhydride or succinic anhydride is fed continuously together with hydrogen, and without further treatment or working-up, over a hydrogenation catalyst.

Maleic anhydride,

HC=CHC(0)OC(0), is derived from a number of sources. Mostly maleic anhydride is produced by passing a mixture of benzene or butane over a vanadium/phosphorous oxide catalyst at about 450° C. Maleic anhydride is also produced as a by-product from the manufacture of phthalic anhydride from napthalene or by the catalytic oxidation of butylenes. Succinic anhydride,

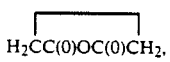
$H_2CC(0)OC(0)CH_2$, may be produced by the dehydration of succinic acid but is most commonly produced by the direct hydrogenation of maleic anhydride.

Typically, the hydrogen ($H_2$) containing gas is commercially pure hydrogen. However, the hydrogen containing gas in addition to hydrogen ($H_2$) may also contain nitrogen ($N_2$), oxygen ($O_2$), any gaseous hydrocarbon (e.g. methane), as well as gaseous oxides of carbon, (e.g. carbon monoxide, carbon dioxide).

Catalyst

The instant process for the hydrogenation of at least one of maleic anhydride or succinic anhydride to produce gamma-butyrolactone and tetrahydrofuran is characterized by the use of a hydrogenation catalyst comprising a catalytically active oxide material and an inert support wherein the catalytically active oxide material is coated upon the inert support.

The catalytically active oxide comprises the mixed oxides of copper, zinc and aluminum. Typically, the catalytically active oxide comprising the mixed oxides of copper, zinc and aluminum is of the general formula:

$Cu_1Zn_bAl_cM_dO_x$ where
M is at least one element selected from Groups IIA thru VA, Group VA, Group VIII, Ag, Au, Groups IIIB thru VIIB, the Lanthanum Series, and Actinium Series of the Period Table of Elements
$0.001 < b < 500$;
$0.001 < c < 500$;
$0 \leq d < 200$; and
x is the number of oxygen atoms necessary to satisfy the valency requirements of the other elements.

As used herein, the Periodic Table of Elements refers to the commonly accepted version as appears in *The Condensed Chemical Dictionary*, 10th Edition, G. G. Hawley, Van-Nostrand Reinhold Company (1981), p. 789. If component "M" is present, preferably "M" is at least one element selected from the group consisting of Group VIII elements and Groups IIIB thru VIIB elements. More preferably M is chromium. Preferably, the catalytically active oxide identified by the above formula contains greater than 10 wt percent of aluminum and more preferably greater than 15 wt percent of aluminum.

The characterization of the catalyst as "a mixed oxide" does not imply that the catalyst cannot contain metallic components. Typically, prior to reduction there are no metallic components in the catalyst. However, it is theorized that the reduction of certain metal oxides (e.g. copper oxide) will produce some metallic (i.e. non-oxide) component in the catalyst composition. Additionally, the catalyst may also contain nitrogen and phosphorus (i.e. where "M" is a Group V element), and compounds containing such elements are typically not referred to as "oxides". Nevertheless such nitrogen and phosphorus containing compositions as described herein will still comprise the mixed oxides of copper, zinc and aluminum and are within the meaning of "catalytically active oxides" or "mixed oxides" as used herein.

Copper chromium containing hydrogenation catalysts are known in the art. The catalytically active oxide shown by the above formula optionally contains chromium, iron, nickel and cobalt; however, an excellent catalyst of the above formula may be produced with no chromium, no iron, no nickel or no cobalt contained in the catalyst.

Typically, the catalytically active oxide of the present invention may be prepared by conventional techniques including coprecipitation techniques such as those described in *Preparation of Catalysts III*, Hoffstadt et al., Elsevier Science Publishers B. V., (1983) pgs. 709–721. In general, this technique comprises coprecipitation of an aqueous metal nitrate solution at elevated temperatures with an alkali or ammonium carbonate or bicarbonate. The precipitated material is then filtered off, washed and then dried at elevated temperatures (120° C.) and calcined at a temperature of 350°–500° C. The catalyst could also be impregnated with one or more promoter elements prior to the calcination step. Alternatively, promoter elements could be incorporated in the precipitation step.

The inert support material may be any material that is not active in the oxidation reaction. The inert support may be selected from a wide choice of materials.

Suitable examples of essentially inert support materials include: silica, alumina, alumina-silica, silicon carbide, titania and zirconia. Especially preferred among these supports are: silica, alumina and alumina-silica. Alundum ® fused-alumina supports are most preferred.

Typically the support material will have a diameter of greater than or equal to about 0.125 inches. Preferred supports have a diameter of about 0.1875 inches to about 0.3125 inches, but there is no upper or lower limitation on the size of the support material other than that dictated by the size of the reactor in which the catalyst is to be utilized.

The support material must be at least partially porous. By this is meant the support material must be susceptible to the penetration of liquid. Preferred support materials are capable of absorbing at least about 1% and more preferably 5% by weight of water based upon the weight of the support. The catalyst may have any shape, such as spheres, rings or irregular shapes which provide a higher surface area per unit weight of support. However, the present invention can be utilized to minimize reactor pressure drop by the use of spherical catalysts. These spherical catalysts are prepared by using a spherical support material and distributing the active catalytic material evenly on the outer surface of the support.

The amount of catalytically active oxide material contained in the catalysts of the present invention is within the range of greater than about 1% to about 50% by weight of the combined support and catalytically active material. Preferred catalysts contain catalytically active material in an amount of about 15% to about 30% by weight of the combined support and catalytically active material. The catalysts may include inert binders.

The preparation of these catalysts can be accomplished by various techniques. The basic method of preparing these catalysts is to partially wet the support material with a liquid. The support should not be wet on the outside surface of the total mass. The support should be dry to the touch. If the support is too wet, the active catalytic material will agglomerate into separate aggregates when coating of the support is attempted. These partially wet supports are then contacted with a powder of the catalytically active material with or without oxide support material and the mixture is gently agitated until the catalyst is formed. The powder of the catalytically active material may have a wide range of particle sizes, but preferably, the particle size for the powder should be less than about 0.3 mm in diameter, and more preferably, less than about 0.15 mm in diameter.

Gentle agitation is most conveniently conducted by placing the partially wet support in a rotating drum and adding the active catalytic material until none is taken up by the support. If a greater loading, that is a more extensive coating, of the support is desired, the partially coated support may again be partially wet with a liquid, and this partially wet, partially coated support is then contacted with a further portion of a powder of the catalytically active material; and the mixture again gently agitated until the catalytic material is taken up by the support. This step may be repeated until the desired loading is achieved.

The liquid used to wet the support may include any inorganic liquid, organic liquid, metal sols or solutions containing metal ions, which would not deleteriously affect the catalytically active material. Examples of such liquids are water, alcohols, acids, ethers, ketones, aldehydes, and the like. Water is the preferred liquid. Examples of metal sols include silica sols, alumina sols, zirconia sols and other metal sols. The use of the metal sols offer an additional benefit in that the metal oxide component of the metal sols serves as a binder for the catalytically active oxide and results in a stronger outer coating of the catalytically active oxide on the support.

Prior to use, the catalyst may be reduced at temperatures between 150°–500° C. by flowing hydrogen, or hydrogen mixed with an inert gas (e.g. nitrogen) over the catalyst. Other reducing gas mixtures may also be used, such as carbon monoxide, carbon monoxide/hydrogen, and carbon monoxide/water. The reduction may be carried out at atmospheric or elevated pressures.

Process Parameters

Typically, sufficient catalyst is packed into a fixed-bed reactor and the reactants passed over and/or through a catalyst bed for continuous operation. At least one of maleic anhydride or succinic anhydride (in the absence of added water) are co-fed with a hydrogen-containing gas over the hydrogenation catalyst, at elevated temperatures and pressures. The hydrogen to anhydride molar feed ratio may vary from about 10:1 to about 1000:1, and is preferably between about 50:1 and 500:1. However, the process conditions should be such as to maintain a vapor phase process.

The hydrogen containing gas can be introduced into the hydrogenation apparatus together with the maleic anhydride or succinic anhydride mixture, co-currently or counter-currently. Typically, the anhydride is vaporized in a hot hydrogen containing gas stream and this mixture is then passed over the hydrogenation catalyst. In order to enhance process economics, unreacted hydrogen discharged from the hydrogenation reaction may be recycled to the hydrogenation furnace.

The quality of the results of the hydrogenation reaction is partially dependent on the throughput of the anhydride-hydrogen mixture over the catalyst. The throughput for the successful performance of the reaction can vary within wide limits. For example, the maleic anhydride or succinic anhydride liquid hourly space velocity (LHSV) is between about 0.01 and 10 per hour, the hydrogen containing gas hourly space velocity (GHSV) is between about 100 to 500,000 per hour. The LHSV and GHSV rates used herein are the feed rates of the reactants prior to vaporization of the anhydride. At these rates the contact time is considerably less than one hour. Preferably contact times are less than 1 minute and more preferably less than 20 seconds. Typical reaction times are between 2 and 10 seconds.

The vaporous feed mixture is contacted with the hydrogenation catalyst at pressures of 1 to 500 atmospheres, preferably at about 1 to 100 atmospheres, more preferably at about 1 to 50 atmospheres hydrogen pressure. Suitable reaction temperatures are 200° C. to 400° C. and are preferably 220° C. to 300° C.

Hydrogenation furnaces of conventional construction can be used for carrying out the process of this invention, provided that they are designed for the requisite temperatures and pressures and are made of acid-resistant material. Further, the process may be carried out in a variety of reactors including fixed-bed and fluid-bed systems.

The reaction products (predominantly tetrahydrofuran and gamma-butyrolactone) are advantageously separated by fractional distillation. By-products which are formed in small amounts or unreacted feed, such as, for example, succinic anhydride are advantageously returned to the hydrogenation stage. Small proportions of acidic by-products in the product can be removed by treatment with alkali before distillation.

Using the process of this invention, maleic anhydride is converted virtually quantitatively (i.e., 100 percent conversion of feed to products and by-products) in a simple reaction, without the build-up of coke or tar inside the reactor. The yields of gamma-butyrolactone and tetrahydrofuran achieved are greater than 90 mole percent, e.g., 91–98 mole percent. The formation of non-utilizable by-products is slight.

Gamma-butyrolactone is an intermediate in the hydrogenation of maleic anhydride or succinic anhydride to tetrahydrofuran. It has been theorized that the existence of succinic anhydride in the reactor strongly inhibits the adsorption of the gamma-butyrolactone onto the catalyst. This means that less tetrahydrofuran is formed when succinic anhydride is concentrated at the catalyst; but as the amount of succinic anhydride decreases, the rapid formation of tetrahydrofuran begins. The use of coated catalysts as described herein reduces the amount of succinic anhydride needed to inhibit the rapid conversion of gamma-butyrolactone to tetrahydrofuran. Consequently, if the reaction is stopped just before the rapid transformation of gamma-butyrolactone to tetrahydrofuran or if the rate at which gammabutyrolactone is transformed to tetrahydrofuran is slowed. then more gamma-butyrolactone will appear in the product. Methods for accomplishing this and controlling the proportions of tetrahydrofuran and gamma-butyrolactone produced include adjusting the process parameters of (i) temperature, and/or (ii) pressure, and/or (iii) maleic anhydride and succinic anhydride throughput, and/or (iv) maleic anhydride and succinic anhydride partial pressure. For example, at the point in the reaction where significant production of both gamma-butyrolactone and tetrahydrofuran are occurring, (i) increasing the temperature, while maintaining other reaction parameters constant, will favor the production of tetrahydrofuran; (ii) increasing the throughput, while maintaining other reaction parameters constant, will favor gamma-butyrolactone production; and (iii) increasing the partial pressure of the anhydride, while maintaining the overall anhydride throughput and the other reaction parameters constant, will favor gamma-butyrolactone production. Consequently, gamma-butyrolactone and tetrahydrofuran are produced by the instant invention in recoverable quantities approaching a 1 to 50 ratio of tetrahydrofuran to gamma-butyrolactone and combined yields of 90 percent or greater.

Although the preceding description is given in terms of a continuous process, if desired, the process of this invention may be carried out in batch mode employing conditions corresponding to those specified above. Without further elaboration, it is believed that one skilled in the art can, using the preceding description, utilize the present invention to its fullest extent.

SPECIFIC EMBODIMENTS

The following preferred embodiments are to be construed as merely illustrative, and not limitative of the remainder of the disclosure in any way whatsoever.

In these examples, selectivities were calculated on a molar $C_4$ basis (i.e. the selectivity is a molar percentage of the $C_4$ feed being converted to a product). The Gas Hourly Space Velocity (GHSV) was calculated using the volume of active catalysts only (i.e. no support volume). "Other" Products include methane, propane, butane, methanol, propanol, butanol and dibutyl ether.

EXAMPLE 1

A commercially available catalyst comprising the mixed oxides of copper, zinc, aluminum and chromium is employed in Example 1. The oxidized form of this catalyst is of the general formula $CuO/ZnO/Al_2O_3/Cr_2O_3$. The nominal compositions of the unreduced catalyst is as follows:

| | |
|---|---|
| Copper Oxide | 40–50 wt % |
| Zinc Oxide | 10–20 wt % |
| Alumina | 20–30 wt % |
| Chrome Oxide | 1–5 wt % |

This catalyst has an empirical formula of $Cu_{1.0}Al_{1.2}Zn_{0.4}Cr_{0.04}O_x$. The above catalytic oxide was obtained in ⅛" pellet form. The pellets were ground to a fine powder.

A 5 g sample of ground catalytic oxide, with particle diameters less than 38 micron, was coated onto 14 g of Alundum ® support. (Obtained from Norton Chemical: Product #SA 5209) as follows: approximately 10 wt % water was added to the Alundum ® support and the mixture was rolled to ensure even absorption of the water. The catalytic oxide powder was then added gradually with rolling between each addition. After all the powder had coated the support material, the combination was rolled for an additional hour. The coated catalyst was then dried at 120° C. and calcined at 450° C.

The coated catalyst, mixed with 15 g of 14/30 mesh quartz chips, was loaded into a 40 cc reactor. The coated catalyst was reduced at 250° C. and atmospheric pressure, with a gas mixture of 5% $H_2$ in $N_2$ flowing over the coated catalyst at a rate of 1 standard liter per minute (SLM). Catalyst testing was carried out at 20–60 atms. and 250°–260° C. Maleic anhydride was introduced at the top of the reactor and vaporized in a counter-current of hydrogen at 155°–200° C. Test results are detailed in Table I below.

TABLE I

| Age, h | T, °C. | H2/MAH | P, atm. | GHSV, $h^{-1}$ | GBL/THF/SAH Ratio |
|---|---|---|---|---|---|
| 33 | 250 | 254 | 40.8 | 38,415 | 2.3/1/0.56 |
| 61 | 255 | 252 | 40.8 | 40,320 | 1.4/1/0.26 |
| 89 | 260 | 257 | 40.8 | 44,910 | 0.19/1/0.1 |
| 157 | 260 | 200 | 40.8 | 35,100 | 2.0/1/0.55 |
| 207 | 260 | 198 | 61.2 | 36,525 | 1.0/1/0.20 |
| 251 | 260 | 206 | 20.4 | 20,625 | 3.2/1/0.51 |

MAH = maleic anhydride  
GBL = gammabutyrolactone  
THF = tetrahydrofuran  
SAH = succinic anhydride

EXAMPLE 2

A coated catalyst as prepared in Example 1 was compared with ⅛" pellets of $CuO/ZnO/Al_2O_3/Cr_2O_3$ catalysts (i.e. no support) mixed with an equal volume of quartz chips. Reaction parameters for the comparison were 40.8 atmospheres and 250° C. The results of the comparison and other data are as shown in Table II.

TABLE II

| | H2/MAH Ratio | GHSV ($h^{-1}$) | Age (h) | Selectivities | | | |
|---|---|---|---|---|---|---|---|
| | | | | GBL | THF | SAH | Other |
| ⅛" Pellets | 299 | 24,000 | 15 | 11.9 | 67.8 | 16.8 | 3.5 |
| Coated Catalyst | 255 | 37,070 | 15 | 42.3 | 50.4 | 5.5 | 1.8 |
| Coated Catalyst | 255 | 38,415 | 33 | 59.0 | 25.7 | 14.4 | 0.9 |

EXAMPLE 3

A coated catalyst as prepared in Example 1 is tested at 2 to 20 atmospheres pressure according to the procedures described in Example 1. The results and various test parameters are shown in Table III below.

TABLE III

| Age (h) | Temp °C. | P (atm) | H2/MAH | GHSV ($h^{-1}$) | Selectivities | | | |
|---|---|---|---|---|---|---|---|---|
| | | | | | GBL | THF | SAH | Other |
| 149 | 260 | 20.4 | 150 | 17,500 | 69.7 | 13.4 | 15.2 | 1.7 |
| 157 | 260 | 5 | 150 | 9,606 | 79.4 | 9.1 | 9.2 | 2.3 |
| 265 | 270 | 5 | 150 | 16,280 | 80.8 | 6.4 | 10.3 | 2.5 |

TABLE III-continued

| Age (h) | Temp °C. | P (atm) | H₂/MAH | GHSV (h⁻¹) | Selectivities GBL | THF | SAH | Other |
|---|---|---|---|---|---|---|---|---|
| 740 | 280 | 2 | 100 | 11,420 | 91.3 | 1.9 | 2.5 | 4.3 |

The above data illustrates that a lower pressures high gamma-butyrolactone yields can be achieved with less coproduction of succinic anhydride.

EXAMPLE 4

A coated catalyst as prepared in Example 1 is tested at 20-60 atmospheres pressure according to the procedures described in Example 1. The results and various test parameters are shown in Table IV below:

| Age (h) | Temp °C. | P (atm) | H₂/MAH | GHSV (h⁻¹) | Selectivities GBL | THF | SAH | Other |
|---|---|---|---|---|---|---|---|---|
| 61 | 255 | 40.8 | 252 | 40,320 | 54.0 | 33.3 | 11.6 | 1.1 |
| 89 | 260 | 40.8 | 257 | 44,910 | 62.0 | 30.3 | 6.1 | 1.6 |
| 157 | 260 | 40.8 | 200 | 35,100 | 55.9 | 27.7 | 15.2 | 1.2 |
| 207 | 260 | 61.2 | 198 | 36,525 | 45.1 | 44.9 | 9.0 | 1.0 |
| 251 | 260 | 20.4 | 206 | 20,625 | 65.2 | 18.8 | 14.2 | 1.8 |

A comparison of line 3 (Age=157 hrs) with line 5 (Age=251 hrs) illustrates that an increase in pressure shifts the reaction equilibrium towards the production of tetrahydrofuran (or conversely a drop in pressure favors the production of gamma-butyrolactone. This point is further verified by a general comparison of the data in Table IV with the data of Table III.

The data clearly demonstrates the superiority of the coated form of the catalyst for production of high yields of both GBL and THF with lower SAH co-production. Further, the results shown in the table do not necessarily represent the optimum catalyst performance. Further improvements in performance may still be possible through adjustment of the process variables within the following ranges: Temperature 230°-290° C., Pressure 1-80 atms., GHSV 10,000-100,000h⁻¹, and MAH LHSV=0.1−5h⁻¹.

The invention claimed is:

1. A continuous process for the preparation of gamma-butyrolactone and tetrahydrofuran comprising catalytically hydrogenating a vaporous mixture of a hydrogen containing gas and at least one of maleic anhydride or succinic anhydride in contact with a catalyst comprising an essentially inert, at least partially porous support, said support having an outer surface, and a catalytically active oxide material coating on said outer surface of said support which strongly adheres to said outer surface of said support, wherein the catalytically active oxide material comprises a mixed oxide catalyst of the formula $$Cu_1Zn_bAl_cM_dO_x$$

wherein

M is at least one element selected from the group consisting of Groups IIA thru VA, Group VIII, Ag, Au, Groups IIIB thru VIIB, the Lanthanum Series, and the Actinium Series;
$0.001 < b < 500$;
$0.001 < c < 500$;
$0 \leq d < 200$; and
x is the number of oxygen atoms necessary to satisfy the valency requirements of the other elements.

2. The process of claim 1, where M is at least one element selected from the group consisting of Group VIII elements and Groups IIIB thru VIIB elements.

3. The process of claim 2, where M is at least one element selected from Group VIII elements.

4. The process of claim 2, where M is chromium.

5. The process of claim 1, wherein the inert support is selected from the group consisting of silica, alumina, aluminasilica, silicon carbide, titania, and zirconia.

6. The process of claim 1, wherein the support has a diameter greater than or equal to about 0.125 inches.

7. The process of claim 6, wherein the support has a diameter between about 0.1875 inches and about 0.3125.

8. The process of claim 1, wherein the coating is between about 1 and about 50 percent by weight of the catalyst.

9. The process of claim 8, wherein the coating is between about 15 and 30 percent by weight of the catalyst.

10. The process of claim 1, wherein the catalyst comprises at least one metal sols.

11. The process of claim 1, wherein the hydrogen to anhydride feed ratio is between about 10 to 1 and 1000 to 1.

12. The process of claim 11, wherein the hydrogen to the anhydride feed ratio is between about 50 to 1 and 500 to 1.

13. The process of claim 1, wherein the hydrogenation is conducted at a pressure about 1 to 100 atmospheres and at a temperature of about 200° C. to 400° C.

14. The process of claim 13, wherein the hydrogenation is conducted at a pressure of about 1 to 50 atmospheres and at a temperature of about 220° C. to 300° C.

* * * * *